United States Patent

Venuti

Patent Number: 5,089,657
Date of Patent: Feb. 18, 1992

[54] NAPHTHALENE ANTI-PSORIATIC AGENTS

[75] Inventor: Michael C. Venuti, San Francisco, Calif.

[73] Assignee: Syntex (U.S.A.) Inc., Palo Alto, Calif.

[21] Appl. No.: 24,426

[22] Filed: Mar. 11, 1987

[51] Int. Cl.⁵ .............................................. C07C 69/00
[52] U.S. Cl. .................................. 560/139; 560/105; 560/107; 260/410.5; 514/550; 514/552; 514/533
[58] Field of Search ...................... 560/139, 105, 107; 260/410.5; 574/550, 552, 533

Primary Examiner—Paul J. Killos
Attorney, Agent, or Firm—Brian Lewis; David A. Lowin; Tom M. Moran

[57] ABSTRACT

Psoriasis in mammals is relieved by topically administering naphthalenes of the formula:

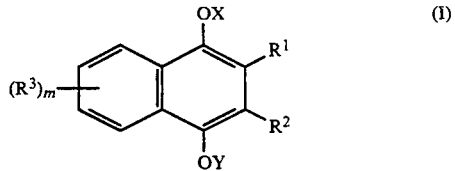

wherein:
$R^1$ is lower alkoxy or optionally substituted phenoxy;
$R^2$ is hydrogen, lower alkyl, optionally substituted phenyl or optionally substituted phenyl-lower-alkyl;
$R^3$ is hydrogen, lower alkyl, lower alkoxy, halo, optionally substituted phenyl, optionally substituted phenyl-lower-alkyl or optionally substituted phenyl-lower-alkoxy, and m is 1 or 2;
X and Y are different and are selected from the group consisting of hydrogen, $R^4$ and -C(O)W, wherein
W is alkyl of one to seven carbon atoms, optionally substituted phenyl or optionally substituted benzyl; and
$R^4$ is lower alkyl or optionally substituted phenyl-lower-alkyl.

41 Claims, No Drawings

NAPHTHALENE ANTI-PSORIATIC AGENTS

BACKGROUND OF THE INVENTION

1. Field of the Invention

The invention relates to naphthalene derivatives which are useful in the treatment of certain dermatological conditions and inhibiting lipoxygenase activity, particularly 5-lipoxygenase activity which makes the compounds useful for topical treatment of inflammatory states. This invention also relates to pharmaceutical compositions useful in relieving the effects of certain chronic recurrent papulosquamous dermatoses, e.g., psoriasis. This invention also relates to a process for preparing compounds of this invention.

2. Related Disclosures

Psoriasis is a skin disease characterized in part by excessive proliferation of cells of the epidermis which remain strongly adherent and build up into a scaley plaque typical of the disease. While currently available therapies, such as corticosteroids, vitamin A derivatives (retinoids), cancer chemotherapeutic agents (methotrexate, razonxane), coal tar and anthralin preparations, and psoralen-u.v. irradiation (PUVA) are effective in controlling the disease to a certain extent, they can cause numerous and sometimes severe undesirable side effects including renal irritation, hepatic toxicity, and erythema.

The compounds 1-hydroxy-2,4-dimethoxynaphthalene, 1-acetoxy-2,4-dimethoxynaphthalene, 1-hydroxy-2,4-diethoxynaphthalene, 1-acetoxy-2,4-diethoxynaphthalene and 1,2-dimethoxy-4-hydroxynaphthalene are known, but no useful biological activity has been ascribed to them. For example, see J. Org. Chem., 34, 2788–90 (1969), J. Org. Chem., 45, 3422–33 (1980) and Liebigs Ann, Chem., 1983, 1886–1900. Certain naphthoquinone derivatives are known to be useful in treating psoriasis. See, for example, U.S. Pat. Nos. 4,229,478, 4,466,981 and 4,593,120 and British Patent No. 1,243,401. Surprisingly, it has been discovered that the compounds of the instant invention area also effective antipsoriatic agents. Compounds of formula (Ic) and (Id), infra, provide prolonged activity in the treatment of psoriasis because of their stability upon application and slow conversion to compounds of formula (Ie) and (If). Further, the compounds of the present invention are more stable in the topical formulations normally used.

SUMMARY

The present invention relates to a pharmaceutical composition in a form suitable for topical administration to mammals comprising a compounds of the formula

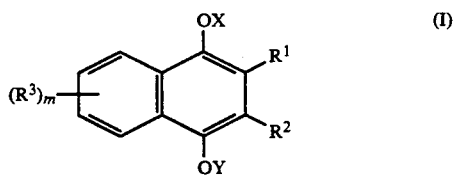

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are selected from the group consisting of hydrogen, $R^4$ and —C(O)W, wherein
  W is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and
  $R^4$ is lower alkyl of one to six carbon atoms or phenyl-lower-alkyl of one to six carbon atoms, wherein the phenyl ring is optionally substituted by one or two substituents chosen from lower alkyl of one to four carbon atoms, lower alkoxy of one to four carbon atoms and halo.

Another aspect of the invention is a method for relieving inflammatory diseases such as the condition of psoriasis in a mammal which comprises topically administering to said mammal an antiinflammatory amount of a compound of formula (I).

Yet another aspect of the invention is the novel compounds of formula (I) wherein $R^1$, $R^2$, $R^3$, $R^4$, X, Y, W and m are as defined above with the proviso that X is not hydrogen or acetyl when $R^1$ is methoxy or ethoxy, $R^2$ and $R^3$ are hydrogen and Y is methyl or ethyl, and Y is not hydrogen when X is methyl, $R^1$ is methoxy and $R^2$ and $R^3$ are hydrogen.

Yet another aspect of the invention is a novel process for preparing compounds of formula (I). Compounds of formula (Ia) and (Ib) infra, which are intermediates for compounds of formula (Ic), (Id), (Ie) and (If) infra, are prepared by carefully controlled hydrolysis of the compound of formula (VII). Compounds of formula (Ic) and (Id) are prepared by reacting compounds of formula (Ia) and (Ib) with the appropriate reactant. Compounds of formula (Ie) and (If) are prepared by hydrolyzing compounds of formula (Ic) and (Id).

DETAILED DESCRIPTION AD PREFERRED EMBODIMENT

It its broadest aspect, the present invention relates to a pharmaceutical composition in a form suitable for topical administration to mammals comprising a compound of the following formula

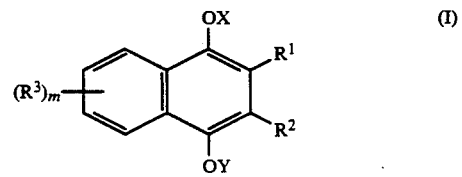

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are selected from the group consisting of hydrogen, $R^4$ and —C(O)W, wherein W is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^4$ is lower alkyl of one to six carbon atoms or phenyl-lower-alkyl of one to six carbon atoms, wherein the phenyl ring is optionally substituted by one or two substituents chosen from lower alkyl of one to four carbon atoms, lower alkoxy of one to four carbon atoms and halo.

The present invention also relates to a method for relieving inflammatory diseases such as the condition of psoriasis in a mammal which comprises topically administering to said mammal an antiinflammatory amount of a compound of formula (I).

Yet another aspect of the invention is the novel compounds of formula (I) wherein $R^1$, $R^2$, $R^3$, $R^4$, X, Y, W and m are as defined above with the proviso that X is not hydrogen or acetyl when $R^1$ is methoxy or ethoxy, $R^2$ and $R^3$ are hydrogen and Y is methyl or ethyl, and Y is not hydrogen when X is methyl, $R^1$ is methoxy and $R^2$ and $R^3$ are hydrogen.

The compounds of formula (I) may be divided into subgroups (Ia), (Ib), (Ic), (Id), (Ie) and (If).

Compounds of subgroup (Ia) and (Ib) are represented by formula (I) wherein either X or Y is hydrogen and the other is —C(O)W wherein $R^1$, $R^2$, $R^3$ and W are as defined above. Within this subgroups it is preferred that W is a sterically hindered group such as i-propyl, i-butyl, optionally substituted phenyl and 2,2-dimethylethyl, with W being 2,2-dimethylethyl and optionally substituted phenyl the most preferred.

Compounds of subgroup (Ic) and (Id) are represented by formula (I) wherein one X or Y is $R^4$ and the other is —C(O)W wherein $R^1$, $R^2$, $R^3$, $R^4$ and W are as defined above. Within this subgroup it is preferred that $R^4$ is lower alkyl of one to three carbon atoms such as methyl, ethyl, n-propyl and i-propyl, with methyl being most preferred.

Compounds of subgroups (Ie) and (If) are represented by formula (I) wherein one X or Y is hydrogen and the other is $R^4$ wherein $R^1$, $R^2$, $R^3$ and $R^4$ are as defined above. Within this subgroup it is preferred that $R^4$ is lower alkyl of one to three carbon atoms such as methyl, ethyl, n-propyl and i-propyl, with methyl being most preferred.

An even more specific embodiment of the instant invention are compounds of formula (I) wherein m is 1 and $R^3$ is at the 6-position and is bromo, chloro, fluoro, cyano, methoxy, ethoxy, n-propoxy, i-propoxy, n-butoxy, and i-butoxy, with chloro being most preferred.

A preferred embodiment of the invention are compounds of formula (I) wherein $R^3$ is hydrogen.

Another embodiment of the invention are compounds wherein m is 2 and the two $R^3$s are at the 6 and 7 positions and are lower alkyl, lower alkoxy or halo with $R^3$ as methyl being preferred.

In the present specification and claims the term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, n-heptyl, 2,2-dimethylbutyl and 3,3-dimethylpentyl. The term "lower alkyl" refers to alkyl groups of one to six carbon atoms as defined above. Examples of "lower alkyl" groups are methyl, ethyl, n-propyl, i-propyl, n-butyl, i-butyl, s-butyl, 2,2-dimethylpropyl and t-hexyl. The term "phenyl-lower-alkyl" refers to an optionally substituted phenyl ring attached to an alkylene chain of one to six carbon atoms. Examples of "phenyl-lower-alkyl" groups are benzyl, 4-chlorophenylethyl, phenyl-n-propyl and 2-methoxyphenyl-n-hexyl.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy. "Phenyl-lower-alkoxy" refers to a phenyl ring attached to an alkylene chain of one to six carbon atoms having bonded thereto an oxygen atom. Examples of "phenyl-lower-alkoxy" are benzyloxy, 4-chlorophenylethoxy, phenyl-n-propoxy and 2-methoxyphenylhexyloxy.

The term "sterically hindered" refers to alkyl groups wherein branching occurs at the carbon adjacent to or one carbon removed from the carbonyl group or to optionally substituted phenyl.

Optionally substituted phenyl refers to a phenyl ring optionally substituted by one or more substituents selected from the group consisting of lower alkyl, lower alkoxy and halo unless otherwise defined.

The term "halo" refers to fluoro, chloro, and bromo.

The compounds of formula (I) are defined to show, in part, $R^1$ as lower alkoxy and $R^4$ as lower alkyl. In this situation, as $R^4$ is always attached to oxygen, it can be readily understood that $R^1$ and —$OR^4$ both represent lower alkoxy.

The compounds of formula (I) exist as three pairs of regioisomers (position isomers) represented by the formulas (Ia) and (Ib), (Ic) and (Id), and (Ie) and (If). The isomers may be separated at any stage of the preparation of (Ia), (Ib), (Ic), (Id), (Ie) and (If), but it is preferred to separate the isomeric mixture of compounds of formula (Ia) and (Ib). The individual isomers of compounds of formula (Ic), (Id), (Ie) or (If) may then be prepared. The isomers may be separated by crystallization, normal or reverse phase HPLC or other partition chromatographic techniques, and the like.

The claims and specification of this patent application are intended to encompass each individual isomer of formula (Ia), (Ib), (Ic), (Id), (Ie) and (If) alone or in combination with its regioisomer, unless specifically designated otherwise.

It is possible that the preparation of compounds of formula (II) where both $R^2$ and $R^3$ are other than hydrogen may give rise to a mixture of two isomers, i.e. the two isomers where $R^2$ is at the 2- or the 3-position of the compound of formula (II). Without separation, this would lead eventually to a mixture of 2- and 3-isomers of the compound of formula (I). In the event that such a mixture is obtained, the isomers may be separated by crystallization, normal or reverse phase HPLC or other partition chromatographic techniques, and the like. The claims and specification of this patent application are intended to encompass each individual isomer of formula (I) alone or in combination with its corresponding isomer, unless specifically designated otherwise.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthalene of formula (I) may be formulated with suitable pharmaceutical vehicles known in the art to form particularly effective topical compositions. An effective amount of the naphthalene compound is about 0.001%w to about 10%w of total formulated composition. The rest of the formulated composition will be about 90%w to about 99.999%w of a suitable excipient which may include pharmaceutically acceptable solvent and other pharmaceutically acceptable additives to form a topically effective pharmaceutical formulation.

A pharmaceutically acceptable solvent is one which is substantially non-toxic and non-irritating under the conditions used any may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats of oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| Water/glycol mixture (15% or more glycol) | 50-99 parts by weight |
| --- | --- |
| Fatty Alcohol | 1-20 |
| Non-ionic Surfactant | 0-10 |
| Mineral Oil | 0-10 |
| Typical Pharmaceutical Adjuvants | 0-5 |
| Active Ingredients | 0.001-10 |

The fatty alcohol, non-ionic surfactant, and other adjuvants are discussed in U.S. Pat. No. 3,934,013 to Poulsen which is incorporated herein by reference.

The naphthalenes of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| White Petrolatum | 40-94 | parts by weight |
| --- | --- | --- |
| Mineral Oil | 5-20 | |
| Glycol Solvent | 1-15 | |
| Surfactant | 0-10 | |
| Stabilizer | 0-10 | |
| Active Ingredients | 0.001-10.0 | |

Other suitable ointment base formulations which employ propylene carbonate are described in U.S. Pat. No. 4,017,615 issued Apr. 12, 1977 by Shastri et al. entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| Active Ingredients | 0.001-10.0 parts by weight |
| --- | --- |
| Propylene Carbonate | 1-10 |
| Solvent | 1-10 |
| Surfactant | 0-10 |
| White Petrolatum | 70-97 |

Suitable solvents, surfactants, stabilizers, etc. are discussed in U.S. Pat. No. 3,934,013 and such are incorporated herein by reference.

A suitable optical "non-classical" anhydrous, water washable "ointment type" base is described in U.S. Pat. No. 3,592,930 to Katz and Neiman, and that patent is incorporated herein by reference. A representative composition of this invention utilizing such as base is as follows:

| Glycol Solvent | 40-35 | parts by weight |
| --- | --- | --- |
| Fatty Alcohol | 15-45 | |
| Compatible Plasticizer | 0-15 | |
| Compatible Coupling Agent | 0-15 | |
| Penetrant | 0-20 | |
| Active Ingredients | 0.001-10.0 | |

Another aspect of the invention is a method for relieving the condition of psoriasis in a mammal by topically administering a composition containing a compound of formula (I) wherein $R^1$, $R^2$, $R^3$, $R^4$, W, X, Y and m are as defined above. Generally, the anti-psoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed hereinabove, which is then placed in contact with the afflicted area(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

The compounds of this invention are also useful to treating mammals having a variety of disease states caused by lipoxygenase activity, particularly 5-lipoxygenase activity.

In vitro lipoxygenase inhibiting activity of the compounds of this invention are determined by the standard Human Polymorphonuclear Leukocytes assay. This assay is a modification of that described by O. Radmark, C. Malmsten, And B. Samuelsson in *FEBS Letter*, 110, 213-215, 1980. In vivo lipoxygenase inhibiting activity of the compounds of this invention are determined by the arachidonic acid mouse ear inflammation assay as described by J. M. Young, D. A. Spires, C. J. Bedord, B. Wagner, S. J. Ballaron and L. M. DeYoung in *Journal of Investigative Dermatology*, 82, 367-371, 1984.

PREPARATION

The compounds of formula (Ia) (Ib), (Ic), (Id), (Ie) and (If) may be prepared as shown in Reaction Sequence I.

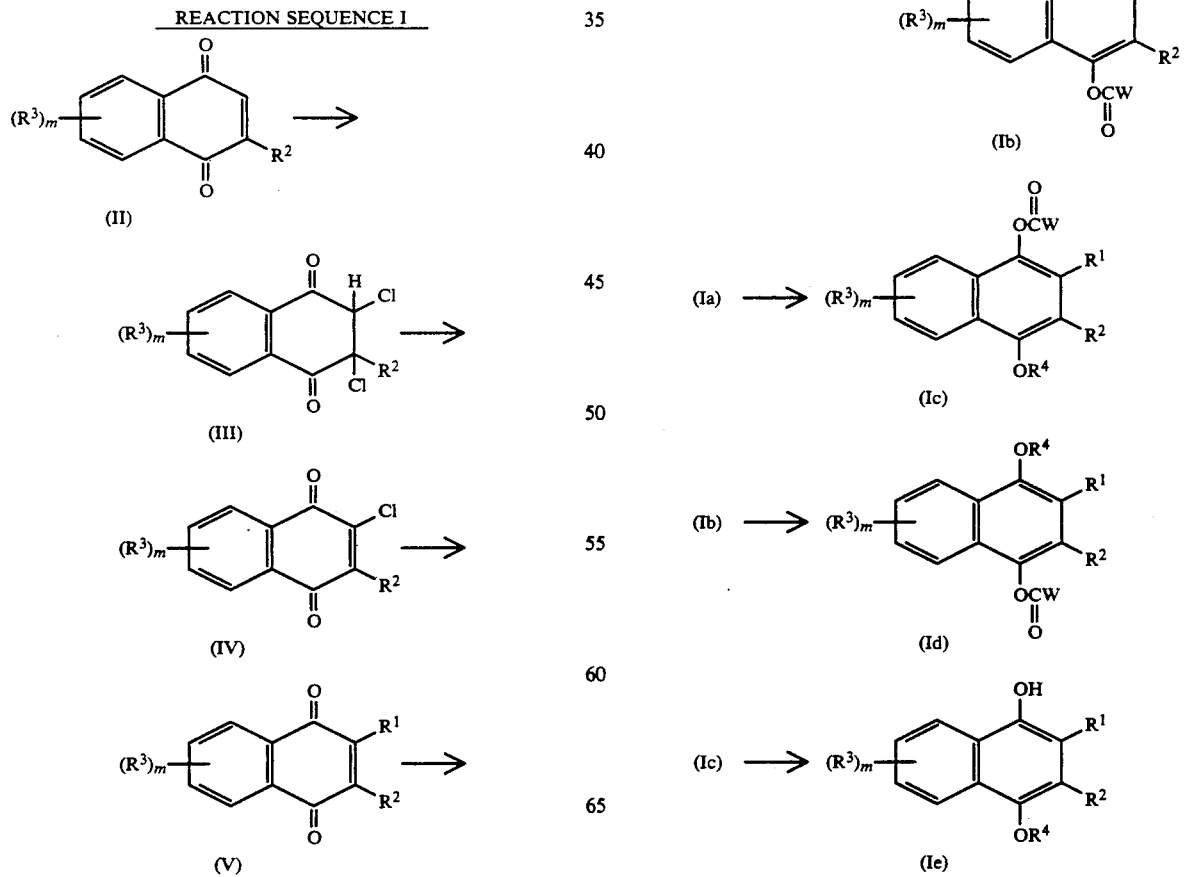

-continued
REACTION SEQUENCE I (Id) ⟶ 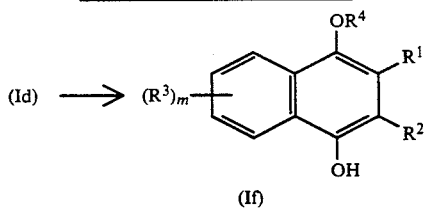

(If)

wherein $R^1$, $R^2$, $R^3$, $R^4$, m and W are as defined above.

The intermediates of formula (II), where $R^2$ is hydrogen and $R^3$ is as defined above are prepared according to the method disclosed in J. Am. Chem. Soc., 70, 3165 (1948) and Ibid., 71, 3615 (1949). A butadiene substituted with the appropriate embodiment of $R^3$ is reacted with 1,4-benzoquinone in a solvent such as acetic acid at a temperature of $-10°$ C. to 30° C., preferably at 25° C. for 24 to 72 hours, preferably from 40 to 48 hours. The 5,8-dihydro derivative of the compound of formula (II) is recovered and treated with an oxidizing agent such as sodium dichromate, sodium nitrite, manganese dioxide and the like to form compounds of formula (II) wherein $R^2$ is hydrogen. Compounds of formula (II) wherein $R^2$ is alkyl, optionally substituted phenyl or phenylalkyl may be prepared by reacting the naphthoquinone of formula (II) wherein $R^2$ is hydrogen with an acid of the formula $R^2COOH$ wherein $R^2$ is as defined above but is other than hydrogen. A solution of the acid and naphthoquinone in acetonitrile and sulfolane in the presence of a metal nitrate, e.g. silver nitrate and the like, is heated to 50°–100° C., preferably to 55°–75° C. A solution of a persulfate salt, e.g. diammonium persulfate, is added dropwise. Compounds of formula (II) wherein $R^2$ is alkyl, optionally substituted phenyl or phenylalkyl are recovered by conventional means such as chromatography.

Compounds of formula (III) are prepared by bubbling chlorine gas into a solution of compound of formula (II) dissolved in a solvent such as glacial acetic acid, nitrobenzene, carbon tetrachloride and the like, preferably glacial acetic acid maintained at about 15° C. The compound of formula (II), which may be isolated by known means, dissolved in a solvent such as acetic acid is treated with a suitable catalyst such as sodium acetate, iodine, iron(III)chloride, dimethylformamide or lower alcohols with heating under reflux for ½ to 4 hours, preferably for 1 to 2 ½ hours to yield compounds of formula (IV).

Compounds of formula (V) are prepared by reacting compound of formula (IV) with an alkali metal alkoxide or phenoxide such as sodium alkoxide or phenoxide, e.g., sodium methoxide or phenoxide in an anhydrous solvent such as methanol, tetrahydrofuran, dimethylformamide and the like, the solvent if an alcohol being chosen according to the length of the alkyl chain on the alkoxy group e.g. sodium methoxide in methanol, sodium ethoxide in ethanol and the like. The reaction mixture is stirred at a temperature of about 0° C. to 60° C., preferably about 20° C. to 30° C., for 3 hours to 24 hours, preferably for 10 to 18 hours. Compounds of formula (V) are recovered by conventional means such as by crystallization.

Compounds of formula (IV) may also be converted to compounds of formula (V), by treatment with an alcoholic solution of a strong base such as potassium hydroxide in methanol and then alkylating the intermediate compound of formula (IX), infra, using the appropriate halide or an alcohol as is described hereinafter under Reaction Sequence II.

Compounds of formula (VII) are prepared from compounds of formula (V) by first hydrogenating to form compounds of formula (VI). The compound of formula (V) is hydrogenated in a hydrogen atmosphere in the presence of a catalyst such as palladium on charcoal, or alternatively using transfer hydrogenation conditions with, for example, cyclohexadiene and a catalyst such as palladium on charcoal. Polar solvents such as tetrahydrofuran, dimethylformamide or ethanol are preferred, most preferably tetrahydrofuran. Alternatively, the compounds of formula (V) are reduced with sodium hydrosulfite in an alcoholic solvent to give the compound of formula (VI).

The compound of formula (VI) is then reacted with an acylating agent such as an appropriate anhydride, for example acetic anhydride, propanoic anhydride, benzoic acid anhydride and the like, preferably acetic anhydride, in the presence of an organic base such as pyridine, triethylamine and the like or an inorganic base such as sodium hydroxide, potassium carbonate, sodium bicarbonate and the like, preferably triethylamine, in an inert solvent such as benzene, acetonitrile, ethyl acetate, tetrahydrofuran, diethyl ether, chloroform, methylene chloride and the like. Acyl halides may also be used to acylate compounds of formula (VI) but acyl anhydrides are preferred. Compounds of formula (VII) are isolated by conventional means, preferably crystallization.

An alternative method for preparing the compounds of formula (V) is depicted in Reaction Sequence II below.

REACTION SEQUENCE II

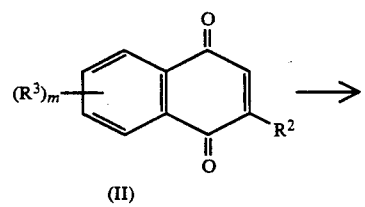

(II)

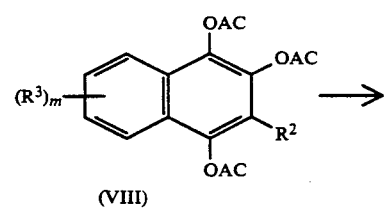

(VIII)

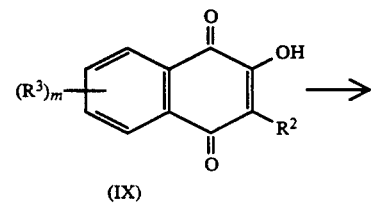

(IX)

-continued
REACTION SEQUENCE II

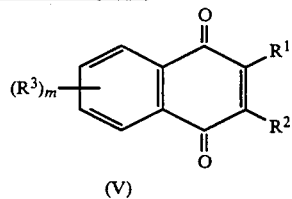

(V)

wherein $R^1$, $R^2$, $R^3$ and m are as defined above.

The compound of formula (VII) is prepared by acylating the compound of formula (II) in the presence of a Lewis acid such as boron trifluoride:etherate or a strong inorganic acid, such as perchloric acid, and the like. This reaction is commonly known as the Theile-Winter reaction. The acylating agent is an acid anhydride such as acetic anhydride, propanoic anhydride and the like, preferably acetic anhydride. The compound of formula (VIII) wherein $R^2$ is hydrogen may be converted to the compound of formula (VIII) wherein $R^2$ is alkyl, optionally substituted phenyl or phenylalkyl by reaction with a peracid anhydride of the formula $(R_2CO_2)_2$ wherein $R^2$ is as defined above but is other than hydrogen. A solution of the unsubstituted compound in a solvent such as glacial acetic acid is heated to 70°–120° C., preferably from 75°–100° C. and an ethereal solution of the anhydride is added dropwise over 1 to 6 hours, preferably over 2 to 4 hours. The compound of formula (VIII) wherein $R^2$ is alkyl, optionally substituted phenyl or phenylalkyl is recovered by precipitation. The compound of formula (VIII) wherein $R^2$ is hydrogen or alkyl, optionally substituted phenyl or phenylalkyl is then hydrolyzed by treatment with an alkali metal alkoxide in an alcohol, such as sodium methoxide in methanol, followed by treatment with aqueous hydrochloric acid to form the compound of formula (IX).

The compound of formula (IX) is then converted to the compound of formula (V) by reaction with an appropriate halide and base.

The compound of formula (IX) is reacted with an alkyl halide, e.g. an alkyl bromide or alkyl iodide, or a phenylalkyl halide, in a solvent such as tetrahydrofuran and the like. A solution of 1,5-diazobicyclo[5.4.0]-undec-5-ene (DBU) in a solvent such as tetrahydrofuran is added dropwise. The precipitate of DBU-hydrogen halide which forms is removed by filtration and the compound of formula (V) is recovered by evaporation.

The compound of formula (V) may also be prepared by reacting the compound of formula (IX) with an alcohol, such as methanol or ethanol. To a solution of the compound of formula (IX) in the appropriate alcohol of formula $R^1H$ is added boron trifluoride etherate. The solution is heated from 50° to 100° C., preferably from 60° to 80° C. for ½ hour to 4 hours, preferably for 1 to 3 hours. The compound of formula (V) is recovered by filtration.

COMPOUNDS OF FORMULA (I)

The compounds of formula (Ia) and (Ib), i.e., compounds wherein either X or Y is hydrogen and the other X or Y is —C(O)W, are prepared from the compounds of formula (VII) by a novel hydrolysis process wherein the pH of the reaction mixture is carefully controlled and maintained at pH 7.5 to 9.5, preferably pH 8-9. If general hydrolysis conditions are employed both ester groups are removed from the compound of formula (VII) to form the compound of formula (VI) which will revert to the 1,4-naphthoquinone under aerobic conditions.

The compound of formula (VII), dissolved in a mixture consisting of a pH 8–9 buffer solution such as a phosphate buffer solution and the like, and a solvent such as acetonitrile, dimethylformamide and the like, is heated to 40° C. to 120° C., preferably to 50° C. to 100° C. for 1 to 15 days, preferably for 2 to 12 days. The reaction is monitored by, e.g., thin layer chromatography. Additional buffer is added, if necessary, to maintain pH 8–9. The compounds of formula (Ia) and (Ib) are recovered by, e.g., extraction and purified by recrystallization. The mixture of compounds of formula (Ia) and (Ib) is separated by preparative high pressure liquid chromatography using silica gel and eluting with suitable solvents, for example anhydrous methanol/hexane.

Compounds of formula (Ic) or (Id) may be prepared by reacting a compound of formula (Ia) or (Ib) respectively with an alkylating agent such as an alkyl tosylate, an alkyl mesylate or an alkyl or phenylalkyl halide such as benzyl bromide, i-propyl bromide, n-butyl bromide, phenylethyl bromide and the like.

To a solution of a compound of formula (Ia) or (Ib) and an alkylating agent such as an alkyl or arylalkyl halide in a solvent such as tetrahydrofuran, dimethylformamide and the like, is added an equivalent amount of an amine base such as 1,8-diazobicyclo[5.4.0]-undec-7-one (DBU). The solution is maintained between 0° C. and 120° C., preferably between room temperature and 60° C., for ½ hour to five hours, preferably for 1 hour to 3 hours. The compound of formula (Ic) or (Id) is recovered by, e.g., evaporation followed by chromatography.

Compounds of formula (Ic) or (Id) may also be prepared by reacting the compound of formula (Ia) or (Ib) with a diazoalkane such as diazomethane, diazoethane, diazophenylmethane and the like.

Compounds of formula (Ic) or (Id) wherein either X or Y is methyl are preferably prepared by reacting compound of formula (Ia) or (Ib) with diazomethane.

A solution of the compound of formula (Ia) or (Ib) in a solvent such as ether is treated with a solution of diazomethane, generated in situ from N-methyl-N-nitroso-p-toluenesulfonamide (Diazald ®), in a solvent such as ether. The compound of formula (Ic) or (Id) is recovered by evaporation followed by flash chromatography over silica gel.

Compounds of formula (Ie) or (If) are prepared from the compounds of formula (Ic) and (Id) by hydrolysis of the ester group —C(O)W. Typically, the compound of formula (Ic) or (Id) is dissolved in a water-miscible solvent such as methanol or ethanol containing a base such as sodium hydroxide or potassium carbonate, optionally in the presence of water, and stirred at a temperature of about 0° C. to 80° C., preferably about 20° C. to 30° C., for about 1 to 24 hours, preferably about 4 to 8 hours. When the reaction is substantially complete, the compounds of formula (Ie) and (If) are separated by conventional means, for example column chromatography.

DBU and Diazald ® are available from, i.a., Aldrich Chemical Co. The alkyl and arylalkyl halides are readily available from, i.a., Aldrich Chemical Co. or may be made by methods well known in the art.

The butadiene intermediate, such as 2-chloro-1,3-butadiene (chloroprene), 2-methyl-1,3-butadiene (isoprene), 2-ethyl-1,3-butadiene, 1-methoxy-1,3-butadiene, 2-phenyl-1,3-butadiene, 1-phenyl-1,3-butadiene and the like are available from, i.a., Pflatiz and Bauer Chemical Co. 2-Bromo-1,3-butadiene and 2-fluoro-1,3-butadiene may be prepared by methods well known in the art, for example, by the methods discussed in J. Am. Chem. Soc., 55 786 (1933) and U.S. Pat. No. 2,401,850, respectively.

The acid anhydrides are commercially available from, i.a., Aldrich Chemical Co. or if not available may be prepared by condensing the appropriate acid in the presence of acetic anhydride or acetyl chloride containing a trace of phosphoric acid. The anhydride is recovered by distillation or crystallization.

An alternative method of preparing compounds of formula (Ie) where $R^1$ is the same as $OR^4$ is from the compound of formula (VI) or (VII) as shown in Reaction Sequence III below.

REACTION SEQUENCE III

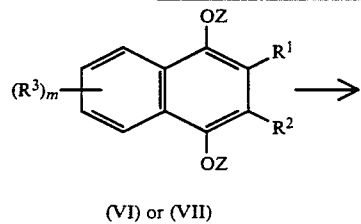

(VI) or (VII)

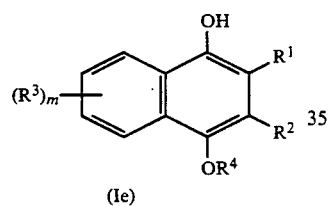

(Ie)

where both Z's are either hydrogen or acetyl and $R^2$, $R^3$, $R^4$ and m are as defined above.

The compound of formula (VI) or (VII) is dissolved in an alcohol of formula $R^1H$ (which in this case is equivalent to the formula $R^4OH$) containing anhydrous hydrochloric acid and the mixture stirred at about 60° C. for about 3 minutes. Ice water is added and the precipitate filtered off and dried under reduced pressure to give the compound of formula (Ie). The reaction is discussed in more detail in J. Org. Chem. 34, 2788 (1969).

In summary, the compounds of formula (I) are made by the procedures below:

(1) The process for preparing compounds of formula (Ia) and (Ib), wherein:

$R^1$ is lower alkoxy or optionally substituted phenoxy, $R^2$ is hydrogen, lower alkyl, optionally substituted phenyl or optionally substituted phenylalkyl;

$R^3$ is hydrogen, lower alkyl, lower alkoxy, halo optionally substituted phenyl, optionally substituted phenyl-lower-alkyl or optionally substituted phenyl-lower-alkoxy and m is 1 or 2; and one of X or Y is —C(O)W when the other X or Y is hydrogen, wherein W is alkyl of one to seven carbon atoms, optionally substituted phenyl or optionally substituted benzyl, which comprises:

hydrolyzing a compound of the formula

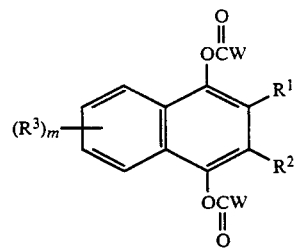

wherein $R^1$, $R^2$, $R^3$, W and m are a defined above, in a buffer solution of pH 8-9.

(2) The process for preparing compounds of formula (Ic) and (Id), wherein:

$R^1$ is lower alkoxy or optionally substituted phenoxy, $R^2$ is hydrogen, lower alkyl, optionally substituted phenyl or optionally substituted phenylalkyl, $R^3$ is hydrogen, lower alkyl, lower alkoxy, halo, optionally substituted phenyl, optionally substituted phenyl-lower-alkyl or optionally substituted phenyl-lower-alkoxy and m is 1 or 2; and one of X or Y is —C(O)W when the other X or Y is $R^4$, wherein W is alkyl of one to seven carbon atoms, optionally substituted phenyl or optionally substituted benzyl, $R^4$ is lower alkyl or optionally substituted phenyl-lower-alkyl, which comprises:

(a) reacting a compound of the formula

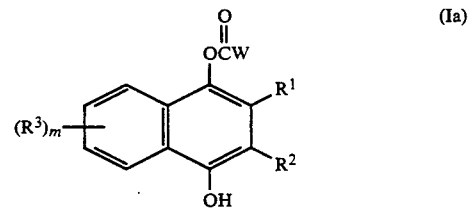

(Ia)

or

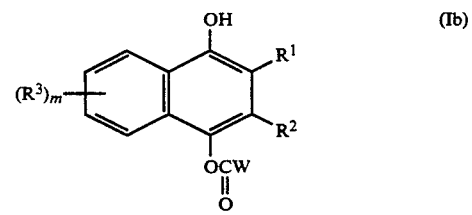

(Ib)

wherein $R^1$, $R^2$, $R^3$, $R^4$, W and m are as defined above, with an appropriate alkylating agent in the presence of a base, or with an appropriate diazoalkane, or (b) reacting a compound of the formula

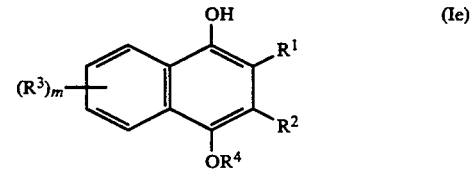

(Ie)

or

-continued

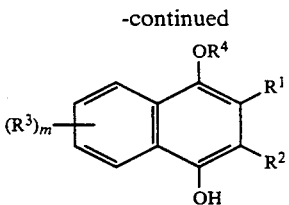
(If)

wherein R¹, R², R³, R⁴ and m are as defined above, with an acylating agent.

(3) Alternatively, a process for the preparation of a compound of the formula (Ie) comprises:
reacting a compound of the formula

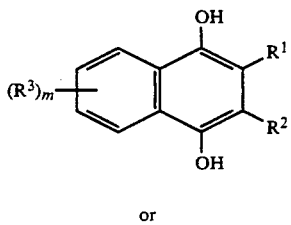
(VI)

or

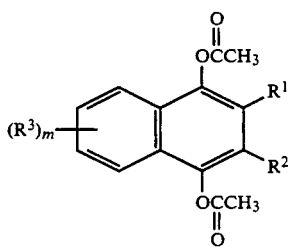
(VI)

wherein R¹, R², R³ and m are as defined above, with an alcohol of formula R¹H and a mineral acid.

(4) The process for preparing compounds of formula (Ie) and (If), wherein:

R¹ is lower alkoxy or optionally substituted phenoxy,

R² is hydrogen, lower alkyl, optionally substituted phenyl or optionally substituted phenylalkyl, R³ is hydrogen, lower alkyl, lower alkoxy, halo, optionally substituted phenyl, optionally substituted phenyl-lower-alkyl or optionally substituted phenyl-lower-alkoxy and m is 1 or 2; and one of X or Y is hydrogen when the other X or Y is R⁴, wherein R⁴ is lower alkyl or optionally substituted phenyl-lower-alkyl, which comprises:

reacting a compound of the formula

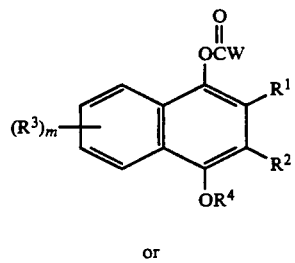
(Ic)

or

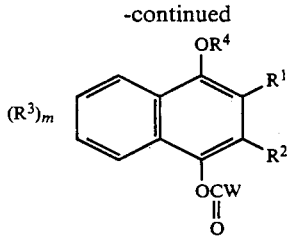
(Id)

wherein R¹, R², R³, R⁴, W and m are as defined above, with a base.

The following specific description is given to enable those skilled in the art to more clearly understand and practice the present invention. It should not be considered as a limitation upon the scope of the invention but merely as illustrative and representative thereof.

PREPARATION 1

A. A solution of 1,4-naphthoquinone (7.91 g), propanoic acid (3.70 g) and silver nitrate (1.53 g) in a mixture of acetonitrile (11.4 mL), sulfolane (34.1 mL) and water (79.5 mL) was heated at 60°–65° C. for 2 hours. A solution of ammonium persulfate (13.7 g) in water (25 mL) was then added dropwise. The mixture was cooled in ice water and extracted with ether. The organic layer was washed with saturated sodium bicarbonate, water and brine then dried, filtered and evaporated. Chromatography over silica gel afforded 2-ethyl-1,4-naphthoquinone, m.p. 87°–88° C.

B. Similarly, using the above procedure but optionally replacing 1,4-naphthoquinone with an appropriately substituted 1,4-naphthoquinone, and optionally replacing propanoic acid with an appropriate carboxylic acid, the following compounds may be prepared:
2-methyl-1,4-naphthoquinone;
2-n-propyl-1,4-naphthoquinone;
2,6-dimethyl-1,4-naphthoquinone;
2-ethyl-5-methyl-1,4-naphthoquinone;
2-sec-butyl-1,4-naphthoquinone;
2-n-pentyl-1,4-naphthoquinone;
2-ethyl-5-fluoro-1,4-naphthoquinone;
3-ethyl-6-methoxy-1,4-naphthoquinone;
2-methyl-6-benzyloxy-1,4-naphthoquinone;
2-ethyl-6-methoxy-1,4-naphthoquinone;
2-methyl-6-fluoro-1,4-naphthoquinone;
2-isopropyl-1,4-naphthoquinone;
2-n-hexyl-1,4-naphthoquinone;
2-methyl-6-chloro-1,4-naphthoquinone;
2,5-dimethyl-1,4-naphthoquinone;
2-methyl-6-phenyl-1,4-naphthoquinone;
2-methyl-5-methoxy-1,4-naphthoquinone;
2-methyl-5-ethoxy-1,4-naphthoquinone;
2-methyl-6-benzyloxy-1,4-naphthoquinone;
2-ethyl-5-chloro-1,4-naphthoquinone;
2-isopropyl-5-phenyl-1,4-naphthoquinone;
2-n-hexyl-6-methyl-1,4-naphthoquinone;
2-n-propyl-6-chloro-1,4-naphthoquinone;
2-n-propyl-6-fluoro-1,4-naphthoquinone;
2-phenyl-1,4-naphthoquinone;
2-t-butyl-1,4-naphthoquinone;
2,6,7-trimethyl-1,4-naphthoquinone; and
2-n-propyl-6-methyl-1,4-naphthoquinone.

PREPARATION 2

Preparation of Compounds of Formula (IV)

A. Chlorine was bubbled through a solution of 1,4-naphthoquinone (39.5 g) in glacial acetic acid maintained at 15° C. by cooling. The precipitated intermediate dichloride was isolated by filtration and then suspended in fresh glacial acetic acid (500 mL). Anhydrous sodium acetate (25 g) was added, and the mixture was brought to reflux. Water was then added, and the mixture was allowed to cool, precipitating 2-chloro-1,4-naphthoquinone, collected by filtration and air drying, m.p. 118° C.

B. 2-Chloro-3-methyl-1,4-naphthoquinone was prepared analogously, except that the intermediate dichloride was isolated as an oil after evaporation, aqueous extraction with ether and evaporation. Conversion of this intermediate using sodium acetate in acetic acid gave 2-chloro-3-methyl-1,4-naphthoquinone, m.p. 155°–156° C.

C. Similarly, using the procedure in paragraph A above, but optionally replacing 1,4-naphthoquinone with an appropriately substituted 1,4-naphthoquinone, the following compounds may be prepared:
2-chloro-3,8-dimethyl-1,4-naphthoquinone;
2-chloro-3-methyl-8-methoxy-1,4-naphthoquinone;
2-chloro-3-methyl-7-benzyloxy-1,4-naphthoquinone;
2-chloro-3-ethyl-8-chloro-1,4-naphthoquinone;
2-chloro-3-isopropyl-8-phenyl-1,4-naphthoquinone;
2-chloro-3-n-hexyl-7-methyl-1,4-naphthoquinone;
2-chloro-3-n-propyl-7-chloro-1,4-naphthoquinone;
2-chloro-3-n-propyl-7-fluoro-1,4-naphthoquinone;
2,6-dichloro-1,4-naphthoquinone;
2,5-dichloro-1,4-naphthoquinone;
2-chloro-6-methoxy-1,4-naphthoquinone;
2-chloro-6-ethoxy-1,4-naphthoquinone;
2-chloro-6-methyl-1,4-naphthoquinone;
2-chloro-6-ethyl-1,4-naphthoquinone;
2-chloro-3-ethyl-1,4-naphthoquinone;
2-chloro-3-n-propyl-1,4-naphthoquinone;
2-chloro-3,7-dimethyl-1,4-naphthoquinone;
2-chloro-3-ethyl-8-methyl-1,4-naphthoquinone;
2-chloro-3-phenyl-1,4-naphthoquinone;
2-chloro-3-isopropyl-1,4-naphthoquinone;
2-chloro-3-sec-butyl-1,4-naphthoquinone;
2-chloro-3-t-butyl-1,4-naphthoquinone;
2-chloro-3-n-pentyl-1,4-naphthoquinone;
2-chloro-3-n-hexyl-1,4-naphthoquinone;
2-chloro-3-ethyl-8-fluoro-1,4-naphthoquinone;
2-chloro-3-methyl-7-phenyl-1,4-naphthoquinone;
2-chloro-6-bromo-1,4-naphthoquinone;
2-chloro-6-fluoro-1,4-naphthoquinone;
2-chloro-6-methyl-1,4-naphthoquinone;
2-chloro-6-i-propyl-1,4-naphthoquinone;
2-chloro-6-phenyl-1,4-naphthoquinone;
2-chloro-6-benzyl-1,4-naphthoquinone;
2-chloro-6,7-dimethyl-1,4-naphthoquinone;
2-chloro-5-methoxy-1,4-naphthoquinone;
2-chloro-5-phenyl-1,4-naphthoquinone;
2,7-dichloro-1,4-naphthoquinone;
2-chloro-7-methyl-1,4-naphthoquinone;
2-chloro-3-ethyl-1,4-naphthoquinone;
2-chloro-3-methyl-1,4-naphthoquinone;
2-chloro-3-ethyl-7-methoxy-1,4-naphthoquinone;
2-chloro-3-methyl-6-ethoxy-1,4-naphthoquinone;
2-chloro-3-methyl-7-benzyloxy-1,4-naphthoquinone;
2,6-dichloro-3-methyl-1,4-naphthoquinone;
2-chloro-3,6,7-trimethyl-1,4-naphthoquinone;
2-chloro-3-n-propyl-7-methyl-1,4-naphthoquinone; and
2,6-dichloro-3-n-propyl-1,4-naphthoquinone.

PREPARATION 3

Preparation of Compounds of Formula (V)

A. A solution of 2-chloro-1,4-naphthoquinone (10.3 g) in tetrahydrofuran (100 mL) was treated with a suspension of sodium ethoxide (3.20 g) in tetrahydrofuran (25 mL) at room temperature. After stirring overnight, the mixture was evaporated, and the residue was taken up in ether. The organic layer was washed with brine, dried, filtered and evaporated. Chromatography over silica gel gave 2-methoxy-1,4-naphthoquinone, m.p. 182°–183° C.

B. Similarly, replacing the 2-chloro-1,4-naphthoquinone with other compounds of formula (IV) and following the above procedure, the following compounds were prepared;
2-ethoxy-1,4-naphthoquinone, m.p. 122°–123° C.;
2-methoxy-3-methyl-1,4-naphthoquinone, m.p. 93°–94° C.;
2-n-propoxy-1,4-naphthoquinone, m.p. 93°–94° C.;
2-isopropoxy-3-methyl-1,4-naphthoquinone, m.p. 114°–115° C.;
2-n-butoxy-1,4-naphthoquinone, m.p. 110°–111° C.;
2-ethoxy-3-methyl-1,4-naphthoquinone, m.p. 67°–68° C.;
2-n-propoxy-3-methyl-1,4-naphthoquinone, oil; and
2-isopropoxy-3-methyl-1,4-naphthoquinone, oil.

C. Similarly, replacing the 2-chloro-1,4-naphthoquinone with other compounds of formula (IV) and following the above procedure, the following compounds are prepared;
2-methoxy-3,8-dimethyl-1,4-naphthoquinone;
2,8-dimethoxy-3-methyl-1,4-naphthoquinone;
2-methoxy-3-methyl-7-benzyloxy-1,4-naphthoquinone;
2-methoxy-3-ethyl-8-chloro-1,4-naphthoquinone;
2-methoxy-3-isopropyl-8-phenyl-1,4-naphthoquinone;
2-methoxy-3-n-hexyl-7-methyl-1,4-naphthoquinone;
2-methoxy-3-n-propyl-7-chloro-1,4-naphthoquinone;
2-methoxy-3-n-propyl-7-fluoro-1,4-naphthoquinone;
2-methoxy-6-chloro-1,4-naphthoquinone;
2-methoxy-5-chloro-1,4-naphthoquinone;
2,6-dimethoxy-1,4-naphthoquinone;
2-methoxy-6-ethoxy-1,4-naphthoquinone;
2-methoxy-6-methyl-1,4-naphthoquinone;
2-methoxy-6-ethyl-1,4-naphthoquinone;
2-methoxy-3-ethyl-1,4-naphthoquinone;
2-methoxy-3-n-propyl-1,4-naphthoquinone;
2-methoxy-3,7-dimethyl-1,4-naphthoquinone;
2-methoxy-3-ethyl-8-methyl-1,4-naphthoquinone;
2-methoxy-3-phenyl-1,4-naphthoquinone;
2-methoxy-3-isopropyl-1,4-naphthoquinone;
2-methoxy-3-sec-butyl-1,4-naphthoquinone;
2-methoxy-3-t-butyl-1,4-naphthoquinone;
2-methoxy-3-n-pentyl-1,4-naphthoquinone;
2-methoxy-3-n-hexyl-1,4-naphthoquinone;
2-methoxy-3-ethyl-8-fluoro-1,4-naphthoquinone;
2-methoxy-3-methyl-7-phenyl-1,4-naphthoquinone;
2-methoxy-6-bromo-1,4-naphthoquinone;
2-methoxy-6-fluoro-1,4-naphthoquinone;
2-methoxy-6-methyl-1,4-naphthoquinone;
2-methoxy-6-i-propyl-1,4-naphthoquinone;
2-methoxy-6-phenyl-1,4-naphthoquinone;
2-methoxy-6-benzyl-1,4-naphthoquinone;
2-methoxy-6,7-dimethyl-1,4-naphthoquinone;

2,5-dimethoxy-1,4-naphthoquinone;
2-methoxy-5-phenyl-1,4-naphthoquinone;
2-methoxy-7-chloro-1,4-naphthoquinone;
2-methoxy-7-methyl-1,4-naphthoquinone;
2-methoxy-3-ethyl-1,4-naphthoquinone;
2-methoxy-3-methyl-1,4-naphthoquinone;
2,7-dimethoxy-3ethyl-1,4-naphthoquinone;
2-methoxy-3-methyl-6-ethoxy-1,4-naphthoquinone;
2-methoxy-3-methyl-7-benzyloxy-1,4-naphthoquinone;
2-methoxy-6-chloro-3-methyl-1,4-naphthoquinone;
2-methoxy-3,6,7-trimethyl-1,4-naphthoquinone;
2-methoxy-3-n-propyl-7-methyl-1,4-naphthoquinone;
2-methoxy-6-chloro-3-n-propyl-1,4-naphthoquinone;
2-ethoxy-3-ethyl-1,4-naphthoquinone;
2-ethoxy-3-n-propyl-1,4-naphthoquinone;
2-ethoxy-3-isobutyl-1,4-naphthoquinone;
2-ethoxy-6-bromo-1,4-naphthoquinone;
2-ethoxy-6-fluoro-1,4-naphthoquinone;
2-ethoxy-6-methyl-1,4-naphthoquinone;
2-ethoxy-6-i-propyl-1,4-naphthoquinone;
2-ethoxy-6-phenyl-1,4-naphthoquinone;
2-ethoxy-6-benzyl-1,4-naphthoquinone;
2-ethoxy-6,7-dimethyl-1,4-naphthoquinone;
2-ethoxy-5-methoxyl-1,4-naphthoquinone;
2-ethoxy-5-phenyl-1,4-naphthoquinone;
2-ethoxy-6-chloro-1,4-naphthoquinone;
2-ethoxy-7-methyl-1,4-naphthoquinone;
2-ethoxy-3-ethyl-5-fluoro-1,4-naphthoquinone;
2-ethoxy-3-methyl-5-phenyl-1,4-naphthoquinone;
2-n-propoxy-3-ethyl-1,4-naphthoquinone;
2-n-propoxy-3-n-propyl-1,4-naphthoquinone;
2-n-propoxy-3-n-hexyl-1,4-naphthoquinone;
2-isopropoxy-3-ethyl-1,4-naphthoquinone;
2-isopropoxy-3-n-propyl-1,4-naphthoquinone;
2-isopropoxy-3-n-hexyl-1,4-naphthoquinone;
2-n-butoxy-3-methyl-1,4-naphthoquinone;
2-n-butoxy-3-ethyl-1,4-naphthoquinone;
2-t-butoxy-1,4-naphthoquinone;
2-sec-butoxy-1,4-naphthoquinone;
2-n-pentyloxy-1,4-naphthoquinone;
2-n-pentyloxy-3-methyl-1,4-naphthoquinone;
2-s-pentyloxy-1,4-naphthoquinone;
2-n-hexyloxy-1,4-naphthoquinone;
2-n-hexyloxy-3-methyl-1,4-naphthoquinone;
2-(2,2-dimethoxylpropoxy)-1,4-naphthoquinone;
2-phenoxy-1,4-naphthoquinone;
2-(4-chorophenoxy)-1,4-naphthoquinone;
2-(4-methoxyphenoxy)-1,4-naphthoquinone;
2-(2,4-dichlorophenoxy)-1,4-naphthoquinone; and
2-(3-methoxyphenoxy)-1,4-naphthoquinone.

PREPARATION 4

(Preparation of a Compound of Formula (VII)

A. A solution of 2-methoxy-1,4-naphthoquinone (20.0 g) in tetrahydrofuran (150 mL) was hydrogenated at atmospheric pressure over Pd-C (10%, 0.5 g) until the calculated amount of hydrogen was absorbed, approximately 4 hours. While still under a blanket of hydrogen, a solution of acetic anhydride (20 mL) and pyridine (18 mL) in tetrahydrofuran (50 mL) was added to the mixture. After stirring for 1 hour, the catalyst was filtered off and solvent evaporated from the filtrate. The residue was dissolved in ether (100 mL), washed with 1M hydrochloric acid (3×50 mL) and then with brine (2×50 mL). The organic layer was dried over sodium sulfate, filtered, and evaporated. Recrystallization from ether afforded 2-methoxy-1,4-diacetyloxynaphthalene, m.p. 135°–136° C.

B. Similarly proceeding as above, substituting the appropriate compound of formula (V) for 2-methoxy-1,4-naphthoquinone, where necessary, and the appropriate acid anhydride, where necessary, for acetic anhydride, the following compounds, for example, were prepared:
2-ethoxy-1,4-diacetyloxynaphthalene, m.p. 64° C.;
2-methoxy-3-methyl-1,4-diacetyloxynaphthalene, m.p. 105°–106° C.;
2-methoxy-1,4-dipropanoyloxynaphthalene, m.p. 91°–92° C.;
2-methoxy-1,4-di(2,2-dimethylpropanoyloxy)-naphthalene, m.p. 111°–112° C.;
6- and 7- chloro-2-methoxy-1,4-diacetyloxynaphthalene, m.p. 77°–78° C.;
2-isobutoxy-1,4-diacetyloxynaphthalene;
2-n-butoxy-1,4-diacetyloxynaphthalene;
2-isopropoxy-1,4-diacetyloxynaphthalene, m.p. 69°–70° C.;
2-n-dodecyloxy-1,4-diacetyloxynaphthalene, m.p. 61°–62° C.;
2-phenoxy-1,4-diacetyloxynaphthalene;
2-methoxy-1,4-di(2,2-dimethylpropanoyloxy)naphthalene; m.p. 109°–110° C.;
2-methoxy-1,4-di-i-butanoyloxynaphthalene, m.p. 79°–80° C.;
2-methoxy-1,4-di-n-butanoyloxynaphthalene, m.p. 68° C.;
2-methoxy-1,4-dibenzoyloxynaphthalene;
2-ethoxy-1,4-dipropanoyloxynaphthalene, m.p. 63°–64° C.;
2-ethoxy-1,4-di-i-butanoyloxynaphthalene;
2-ethoxy-1,4-di(2,2-dimethylpropanoyloxy)naphthalene, m.p. 78°–79° C.; and
2-ethoxy-1,4-dibenzoyloxynaphthalene, m.p. 172°–173° C.

C. Similarly proceeding as above, substituting the appropriate compound of formula (V) for 2-methoxy-1,4-naphthoquinone, where necessary, and the appropriate acid anhydride, where necessary, for acetic anhydride, the following compounds, for example, are prepared:
2-methoxy-3,8-dimethyl-1,4-diacetyloxynaphthalene;
2,8-dimethoxy-3-methyl-1,4-diacetyloxynaphthalene;
2-methoxy-3-methyl-7-benzyloxy-1,4-diacetyloxynaphthalene;
2-methoxy-3-ethyl-8-chloro-1,4-diacetyloxynaphthalene;
2-methoxy-3-isopropyl-8-phenyl-1,4-diacetyloxynaphthalene;
2-methoxy-3-n-hexyl-7-methyl-1,4-diacetyloxynaphthalene;
2-methoxy-3-n-propyl-7-chloro-1,4-diacetyloxynaphthalene;
2-methoxy-3-n-propyl-7-fluoro-1,4-diacetyloxynaphthalene;
2-methoxy-6-chloro-1,4-diacetyloxynaphthalene;
2-methoxy-5-chloro-1,4-diacetyloxynaphthalene;
2,6-dimethoxy-1,4-diacetyloxynaphthalene;
2-methoxy-6-ethoxy-1,4-diacetyloxynaphthalene;
2-methoxy-6-methyl-1,4-diacetyloxynaphthalene;
2-methoxy-6-ethyl-1,4-diacetyloxynaphthalene;
2-methoxy-3-ethyl-1,4-diacetyloxynaphthalene;
2-methoxy-3-n-propyl-1,4-diacetyloxynaphthalene;
2-methoxy-3,7-dimethyl-1,4-diacetyloxynaphthalene;

2-methoxy-3-ethyl-8-methyl-1,4-diacetyloxynaphthalene;
2-methoxy-3-phenyl-1,4-diacetyloxynaphthalene;
2-methoxy-3-isopropyl-1,4-diacetyloxynaphthalene;
2-methoxy-3-sec-butyl-1,4-diacetyloxynaphthalene;
2-methoxy-3-t-butyl-1,4-diacetyloxynaphthalene;
2-methoxy-3-n-pentyl-1,4-diacetyloxynaphthalene;
2-methoxy-3-n-hexyl-1,4-diacetyloxynaphthalene;
2-methoxy-3-ethyl-8-fluoro-1,4-diacetyloxynaphthalene;
2-methoxy-3-methyl-7-phenyl-1,4-diacetyloxynaphthalene;
2-methoxy-6-bromo-1,4-diacetyloxynaphthalene;
2-methoxy-6-fluoro-1,4-diacetyloxynaphthalene;
2-methoxy-6-methyl-1,4-diacetyloxynaphthalene;
2-methoxy-6-i-propyl-1,4-diacetyloxynaphthalene;
2-methoxy-6-phenyl-1,4-diacetyloxynaphthalene;
2-methoxy-6-benzyl-1,4-diacetyloxynaphthalene;
2-methoxy-6,7-dimethyl-1,4-diacetyloxynaphthalene;
2,5-dimethoxy-1,4-diacetyloxynaphthalene;
2-methoxy-5-phenyl-1,4-diacetyloxynaphthalene;
2-methoxy-7-chloro-1,4-diacetyloxynaphthalene;
2-methoxy-7-methyl-1,4-diacetyloxynaphthalene;
2-methoxy-3-ethyl-1,4-diacetyloxynaphthalene;
2-methoxy-3-methyl-1,4-diacetyloxynaphthalene;
2,7-dimethoxy-3-ethyl-1,4-diacetyloxynaphthalene;
2-methoxy-3-methyl-6-ethoxy-1,4-diacetyloxynaphthalene;
2-methoxy-3-methyl-7-benzyloxy-1,4-diacetyloxynaphthalene;
2-methoxy-6-chloro-3-methyl-1,4-diacetyloxynaphthalene;
2-methoxy-3,6,7-trimethyl-1,4-diacetyloxynaphthalene;
2-methoxy-3-n-propyl-7-methyl-1,4-diacetyloxynaphthalene;
2-methoxy-6-chloro-3-n-propyl-1,4-diacetyloxynaphthalene;
2-ethoxy-3-methyl-1,4-diacetyloxynaphthalene;
2-ethoxy-3-ethyl-1,4-diacetyloxynaphthalene;
2-ethoxy-3-n-propyl-1,4-diacetyloxynaphthalene;
2-ethoxy-3-isobutyl-1,4-diacetyloxynaphthalene;
2-ethoxy-6-bromo-1,4-diacetyloxynaphthalene;
2-ethoxy-6-fluoro-1,4-diacetyloxynaphthalene;
2-ethoxy-6-methyl-1,4-diacetyloxynaphthalene;
2-ethoxy-6-i-propyl-1,4-diacetyloxynaphthalene;
2-ethoxy-6-phenyl-1,4-diacetyloxynaphthalene;
2-ethoxy-6-benzyl-1,4-diacetyloxynaphthalene;
2-ethoxy-6,7-dimethyl-1,4-diacetyloxynaphthalene;
2-ethoxy-5-methoxy-1,4-diacetyloxynaphthalene;
2-ethoxy-5-phenyl-1,4-diacetyloxynaphthalene;
2-ethoxy-6-chloro-1,4-diacetyloxynaphthalene;
2-ethoxy-7-methyl-1,4-diacetyloxynaphthalene;
2-ethoxy-3-ethyl-5-fluoro-1,4-diacetyloxynaphthalene;
2-ethoxy-3-methyl-5-phenyl-1,4-diacetyloxynaphthalene;
2-n-propoxy-1,4-diacetyloxynaphthalene;
2-n-propoxy-3-methyl-1,4-diacetyloxynaphthalene;
2-n-propoxy-3-ethyl-1,4-diacetyloxynaphthalene;
2-n-propoxy-3-n-propyl-1,4-diacetyloxynaphthalene;
2-n-butoxy-1,4-diacetyloxynaphthalene;
2-n-butoxy-3-methyl-1,4-diacetyloxynaphthalene;
2-n-butoxy-3-ethyl-1,4-diacetyloxynaphthalene;
2-sec-butoxy-1,4-diacetyloxynaphthalene;
2-t-butoxy-1,4-diacetyloxynaphthalene;
2-n-pentyloxy-1,4-diacetyloxynaphthalene;
2-n-pentyloxy-3-methyl-1,4-diacetyloxynaphthalene;
2-s-pentyloxy-1,4-diacetyloxynaphthalene;
2-n-hexyloxy-1,4-diacetyloxynaphthalene;
2-n-hexyloxy-3-methyl-1,4-diacetyloxynaphthalene;
2-(2,2-dimethylpropoxy)-1,4-diacetyloxynaphthalene;
2-(4-chlorophenoxy)-1,4-diacetyloxynaphthalene;
2-(4-methoxyphenoxy)-1,4-diacetyloxynaphthalene;
2-(2,4-dichlorophenoxy)-1,4-diacetyloxynaphthalene;
2-(3-methylphenoxy)-1,4-diacetyloxynaphthalene;
2-methoxy-1,4-dipropanoyloxynaphthalene;
2-methoxy-1,4-dibutanoyloxynaphthalene;
2-methoxy-1,4-dihexanoyloxynaphthalene;
2-methoxy-3-methyl-1,4-dipropanoyloxynaphthalene;
2-ethoxy-1,4-dipropanoyloxynaphthalene;
2-ethoxy-1,4-dibutanoyloxynaphthalene;
2-ethoxy-1,4-dihexanoyloxynaphthalene;
2-ethoxy-3-methyl-1,4-dipropanoyloxynaphthalene; and
2-phenoxy-1,4-dibenzoyloxynaphthalene.

EXAMPLE I (Preparation of a Compound of Formula (Ia) and (Ib))

A. Ten grams of 2-methoxy-1,4-diacetyloxynaphthalene, 150 ml of 0.05 M, pH 8, phosphate buffer solution and 150 ml of acetonitrile are heated at 80° C. for 10 days. The reaction is monitored by TLC. Additional disodium hydrogen phosphate is added to maintain the reaction mixture at pH 8. The reaction mixture is cooled and solvent evaporated and the resultant residue is extracted with ethyl acetate (3X), washed with 1 M HCl (2X) and brine (2X). The solution is dried over sodium sulfate, filtered and evaporated. The residue is an isomeric mixture from which 1-hydroxy-2-methoxy-4-acetyloxynaphthalene and 1-acetyloxy-2-methoxy-4-hydroxynaphthalene are separated by preparative HPLC on silica gel, eluting with 4% anhydrous methanol is hexane.

B. Similarly, proceeding as in Part A above, substituting the appropriate compound of formula (VII) for 2-methoxy-1,4-diacetyloxnaphthalene the following compounds of formula (Ia) and (Ib) are prepared:
1-acetyloxy-2-ethoxy-4-hydroxynaphthalene;
1-hydroxy-2-ethoxy-4-acetyloxynaphthalene;
1-acetyloxy-2-methoxy-3-methyl-4-hydroxynaphthalene;
1-hydroxy-2-methoxy-3-methyl-4-acetyloxynaphthalene;
1-acetyloxy-2-methoxy-3-ethyl-4-hydroxynaphthalene;
1-hydroxy-2-methoxy-3-ethyl-4-acetyloxynaphthalene;
1-acetyloxy-2-methoxy-3-isobutyl-4-hydroxynaphthalene;
1-hydroxy-2-methoxy-3-isobutyl-4-acetyloxynaphthalene;
1-acetyloxy-2-methoxy-3-n-hexyl-4-hydroxynaphthalene;
1-hydroxy-2-methoxy-3-n-hexyl-4-acetyloxynaphthalene;
1-acetyloxy-2-methoxy-6-bromo-4-hydroxynaphthalene;
1-hydroxy-2-methoxy-6-bromo-4-acetyloxynaphthalene;
1-acetyloxy-2-methoxy-6-fluoro-4-hydroxynaphthalene;
1-hydroxy-2-methoxy-6-fluoro-4-acetyloxynaphthalene;
1-acetyloxy-2-methoxy-6-methyl-4-hydroxynaphthalene;
1-hydroxy-2-methoxy-6-methyl-4-acetyloxynaphthalene;

1-acetyloxy-2-methoxy-6-i-propyl-4-hydroxynaphthalene;
1-hydroxy-2-methoxy-6-i-propyl-4-acetyloxynaphthalene;
1-acetyloxy-2-methoxy-3-t-butyl-4-hydroxynaphthalene;
1-hydroxy-2-methoxy-3-t-butyl-4-acetyloxynaphthalene;
1-acetyloxy-2-methoxy-6-phenyl-4-hydroxynaphthalene;
1-hydroxy-2-methoxy-6-phenyl-4-acetyloxynaphthalene;
1-acetyloxy-2-methoxy-6-benzyl-4-hydroxynaphthalene;
1-hydroxy-2-methoxy-6-benzyl-4-acetyloxynaphthalene;
1-acetyloxy-2-methoxy-6,7-dimethyl-4-hydroxynaphthalene;
1-hydroxy-2-methoxy-6,7-dimethyl-4-acetyloxynaphthalene;
1-acetyloxy-2,5-dimethoxy-4-hydroxynaphthalene;
1-hydroxy-2,5-dimethoxy-4-acetyloxynaphthalene;
1-acetyloxy-2-methoxy-5-phenyl-4-hydroxynaphthalene;
1-hydroxy-2-methoxy-5-phenyl-4-acetyloxynaphthalene;
1-acetyloxy-2-methoxy-6-chloro-4-hydroxynaphthalene;
1-hydroxy-2-methoxy-6-chloro-4-acetyloxynaphthalene;
1-acetyloxy-2-methoxy-3-ethyl-5-fluoro-4-hydroxynaphthalene
1-hydroxy-2-methoxy-3-ethyl-5-fluoro-4acetyloxynaphthalene;
1-acetyloxy-2-methoxy-3-methyl-5-phenyl-4-hydroxynaphthalene;
1-hydroxy-2-methoxy-3-methyl-5-phenyl-4acetyloxynaphthalene;
1-acetyloxy-2-methoxy-3-ethyl-6-methoxy-4-hydroxynaphthalene;
1-hydroxy-2-methoxy-3-ethyl-6-methoxy-4-acetyloxynaphthalene;
1-acetyloxy-2-methoxy-3-methyl-6-ethoxy-4-hydroxynaphthalene;
1-hydroxy-2-methoxy-3-methyl-6-ethoxy-4-acetyloxynaphthalene;
1-acetyloxy-2-methoxy-3-methyl-6-benzyloxy-4-hydroxynaphthalene;
1-hydroxy-2-methoxy-3-methyl-6-benzyloxy-4-acetyloxynaphthalene;
1-acetyloxy-2-methoxy-3-methyl-6-chloro-4-hydroxynaphthalene;
1-hydroxy-2-methoxy-3-methyl-6-chloro-4-acetyloxynaphthalene;
1-acetyloxy-2-methoxy-3-ethyl-6-methoxy-4-hydroxynaphthalene;
1-hydroxy-2-methoxy-3-ethyl-6-methoxy-4-acetyloxynaphthalene;
1-acetyloxy-2-methoxy-5-fluoro-3-methyl-4-hydroxynaphthalene;
1-hydroxy-2-methoxy-5-fluoro-3-methyl-4-acetyloxynaphthalene;
1-acetyloxy-2-methoxy-3,6,7-trimethyl-4-hydroxynaphthalene;
1-hydroxy-2-methoxy-3,6,7-trimethyl-4-acetyloxynaphthalene;
1-acetyloxy-2-methoxy-3-n-propyl-6-methoxy-4-hydroxynaphthalene;
1-hydroxy-2-methoxy-3-n-propyl-6-methyl-4-acetyloxynaphthalene;
1-acetyloxy-2-methoxy-3-n-propyl-6-chloro-4-hydroxynaphthalene;
1-hydroxy-2-methoxy-3-n-propyl-6-chloro-4-acetyloxynaphthalene;
1-acetyloxy-2-ethoxy-4-hydroxynaphthalene;
1-hydroxy-2-ethoxy-4-acetyloxynaphthalene;
1-acetyloxy-2-ethoxy-3-methyl-4-hydroxynaphthalene;
1-hydroxy-2-ethoxy-3-methyl-4-acetyloxynaphthalene;
1-propanoyloxy-2-ethoxy-3-ethyl-4-hydroxynaphthalene;
1-hydroxy-2-ethoxy-3-ethyl-4-propanoyloxynaphthalene;
1-propanoyloxy-2-ethoxy-3-n-propyl-4-hydroxynaphthalene;
1-hydroxy-2-ethoxy-3-n-propyl-4-propanoyloxynaphthalene;
1-propanoyloxy-2-ethoxy-3-isobutyl-4-hydroxynaphthalene;
1-hydroxy-2-ethoxy-3-isobutyl-4-propanoyloxynaphthalene;
1-propanoyloxy-2-ethoxy-6-bromo-4-hydroxynaphthalene;
1-hydroxy-2-ethoxy-6-bromo-4-propanoyloxynaphthalene;
1-n-butanoyloxy-2-ethoxy-6-fluoro-4-hydroxynaphthalene;
1-hydroxy-2-ethoxy-6-fluoro-4-n-butanoyloxynaphthalene;
1-n-butanoyloxy-2-ethoxy-6-methoxy-4-hydroxynaphthalene;
1-hydroxy-2-ethoxy-6-methyl-4-n-butanoyloxynaphthalene;
1-(2-methoxylpentanoyl)oxy-2-ethoxy-6-i-propyl-4-hydroxynaphthalene;
1-hydroxy-2-ethoxy-6-i-propyl-4-(2-methylpentanoyl)oxynaphthalene;
1-(2-methoxypentanoyl)oxy-2-ethoxy-6-phenyl-4-hydroxynaphthalene;
1-hydroxy-2-ethoxy-6-phenyl-4-(2-methylpentanoyl)oxynaphthalene;
1-n-heptanoyloxy-2-ethoxy-6-benzyl-4-hydroxynaphthalene;
1-hydroxy-2-ethoxy-6-benzyl-4-n-heptanoyloxynaphthalene;
1-hydroxy-2-ethoxy-6,7-dimethyl-4n-heptanoyloxynaphthalene;
1-(2,2-dimethylpropanoyl)oxy-2-ethoxy-5-methoxy-4-hydroxynaphthalene;
1-hydroxy-2-ethoxy-5-methoxy-4-(2,2-dimethoylpropanoyl)oxynaphthalene;
1-(2,2-dimethylpropanoyl)oxy-2-ethoxy-5-phenyl-4-hydroxynaphthalene;
1-hydroxy-2-ethoxy-5-phenyl-4-(2,2-dimethylpropanoyl)-oxynaphthalene;
1-acetyloxy-2-ethoxy-6-chloro-4-hydroxynaphthalene;
1-hydroxy-2-ethoxy-6-chloro-4-acetyloxynaphthalene;
1-acetyloxy-2-ethoxy-7-methyl-4-hydroxynaphthalene;
1-hydroxy-2-ethoxy-7-methyl-4-acetyloxynaphthalene;
1-acetyloxy-2-ethoxy-3-ethyl-5-fluoro-4-hydroxynaphthalene;
1-hydroxy-2-ethoxy-3-ethyl-5-fluoro-4-acetyloxynaphthalene;
1-acetyloxy-2-ethoxy-3-methyl-5-phenyl-4-hydroxynaphthalene;
1-hydroxy-2-ethoxy-3-methyl-5-phenyl-4-acetyloxynaphthalene;

1-acetyloxy-2-n-propoxy-4-hydroxynaphthalene;
1-hydroxy-2-n-propoxy-4-acetyloxynaphthalene;
1-acetyloxy-2-n-propoxy-3-methyl-4-hydroxynaphthalene;
1-hydroxy-2-n-propoxy-3-methyl-4-acetyloxynaphthalene;
1-acetyloxy-2-n-butoxy-4-hydroxynaphthalene;
1-hydroxy-2-n-butoxy-4-acetyloxynaphthalene;
1-acetyloxy-2-t-butoxy-4-hydroxynaphthalene;
1-hydroxy-2-t-butoxy-4-acetyloxynaphthalene;
1-acetyloxy-2-hexyloxy-4-hydroxynaphthalene;
1-hydroxy-2-n-hexyloxy-4-acetyloxynaphthalene;
1-acetyloxy-2-phenoxy-4-hydroxynaphthalene;
1-hydroxy-2-phenyl-4-acetyloxynaphthalene;
1-acetyloxy-2-(4-chlorophenoxy)-4-hydroxynaphthalene;
1-hydroxy-2-(4-chlorophenoxy)-4-hydroxynaphthalene;
1-propionoyloxy-2-methoxy-4-hydroxynaphthalene;
1-hydroxy-2-methoxy-4-propionoyloxynaphthalene;
1-butanoyloxy-2-methoxy-4-hydroxynaphthalene;
1hydroxy-2-methoxy-4-butanoyloxynaphthalene;
1-hexanoyloxy-2-methoxy-4-hydroxynaphthalene;
1-hydroxy-2-methoxy-4-hexanoyloxynaphthalene;
1-propanoyloxy-2-methoxy-3-methyl-4-hydroxynaphthalene;
1-hydroxy-2-methoxy-3-methyl-4-propanoyloxynaphthalene;
1-propanoyloxy-2-ethoxy-4-hydroxynaphthalene;
1-hydroxy-2-ethoxy-4-propanoyloxynaphthalene;
1-butanoyloxy-2-ethoxy-4-hydroxynaphthalene;
1-hydroxy-2-ethoxy-4-butanoyloxynaphthalene;
1-hexanoyloxy-2-ethoxy-4-hydroxynaphthalene;
1-hydroxy-2-ethoxy-4-hexanoyloxynaphthalene;
1-propanoyloxy-2-propoxy-3-methyl-4-hydroxynaphthalene; and
1-hydroxy-2-propoxy-3-methyl-4-propanoyloxynaphthalene.

EXAMPLE 2

(Preparation of Compounds of Formula (Ic) and (Id) Where One of X and Y is $R^4$ and the Other X or Y is C(O)W).

A. A solution of 1-acetyloxy-2-methoxy-4-hydroxynaphthalene (23.2 g) and methyl iodide (6.4 mL) in tetrahydrofuran (250 mL) was treated dropwise with a solution of DBU (16.5 mL) in tetrahydrofuran (50 mL). The resulting precipitate of DBU.HI was removed by filtration, and the filtrate evaporated. Recrystallization from methanol gave 1-acetyloxy-2,4-dimethoxynaphthalene, m.p. 116°–117° C.

B. Similarly, optionally replacing 1-acetyloxy-2-methoxy-4-hydroxynaphthalene with an appropriate compound of formula (Ia) and optionally replacing methyl iodide with an appropriate alkylating agent, and following the procedure of paragraph A above, the following compounds of formula (Ic) were prepared.
1-(2,2-dimethylpropanoyloxy)-2,4-dimethoxynaphthalene, m.p. 65°–66° C.;
1-propanoyloxy-2,4-dimethoxynaphthalene, m.p. 83°–84° C.;
1-benzoyloxy-2,4-dimethoxynaphthalene, m.p. 129°–130° C.;
1-propanoyloxy-2,4-diethoxynaphthalene, m.p. 85°–86° C.;
1-acetyloxy-2,4-diethoxynaphthalene, m.p. 114°–115° C.;
1-(2,2-dimethylpropanoyloxy)-2,4-diethoxynaphthalene, m.p. 117°–118° C; and
1-benzoyloxy-2,4-diethoxynaphthalene, m.p. 139°–140° C.

C. Similarly, optionally replacing 1-acetyloxy-2-methoxy-4-hydroxynaphthalene with an appropriate compound of formula (Ia) or (Ib) or optionally replacing methyl iodide with an appropriate alkylating agent, and following the procedure of paragraph A above, the following compounds of formula (Ic) and (Id) are prepared:
1,2-diethoxy-4-propanoyloxynaphthalene;
1,2-diethoxy-4-acetyloxynaphthalene;
1,2-diethoxy-4-(2,2-dimethoylpropionyloxy)naphthalene;
1,2-diethoxy-4-benzoyloxynaphthalene;
1-acetyloxy-2-methoxy-4-ethoxynaphthalene;
1-ethoxy-2-methoxy-4-acetyloxynaphthalene;
1-acetyloxy-2-ethoxy-4-methoxynaphthalene;
1-ethoxy-2-methoxy-4-acetyloxynaphthalene;
1-acetyloxy-2-methoxy-4-propoxynaphthalene;
1-propoxy-2-methoxy-4-acetyloxynaphthalene;
1-acetyloxy-2,4-di-n-butoxynaphthalene;
1,2-di-n-butoxy-4-acetyloxynaphthalene;
1-acetyloxy-2-methoxy-4-n-hexyloxynaphthalene;
1-n-hexyloxy-2-methoxy-4-acetyloxynaphthalene;
1-acetyloxy-2,4-dimethoxy-6-chloronaphthalene;
1,2-dimethoxy-4-acetyloxy-6-chloronaphthalene;
1-n-hexanoyloxy-2,4-dimethoxynaphthalene;
1,2-dimethoxy-4-n-hexanoyloxynaphthalene;
1-phenylacetyloxy-2,4-dimethoxynaphthalene;
1,2-dimethoxy-4-phenylacetyloxynaphthalene;
1-propanoyloxy-2,4-diethoxy-6-chloronaphthalene;
1,2-diethoxy-4-propanoyloxy-6-chloronaphthalene;
1-propanoyloxy-2-ethoxy-4-propoxynaphthalene;
1-propoxy-2-ethoxy-4-propanoyloxynaphthalene;
1-acetyloxy-2,4-dimethoxy-3-methylnaphthalene;
1,2-dimethoxy-3-methyl-4-acetyloxynaphthalene;
1-acetyloxy-2,4-dimethoxy-3-n-butylnaphthalene;
1,2-dimethoxy-3-n-butyl-4-acetyloxynaphthalene;
1-acetyloxy-2,4-dimethoxy-3-methyl-6-chloronaphthalene;
1,2-dimethoxy-3-methyl-4-acetyloxy-6-chloronaphthalene;
1-acetyloxy-2,4-dimethoxy-3-n-butyl-5-ethoxynaphthalene
1,2-dimethoxy-3-n-butyl-4-acetyloxy-5-ethoxynaphthalene
1-acetyloxy-2,4-dimethoxy-3-t-butylnaphthalene
1,2-dimethoxy-3-t-butyl-4-acetyloxynaphthalene
1-acetyloxy-2,4-diethoxy-3-methylnaphthalene;
1,2-diethoxy-3-methyl-4-acetyloxynaphthalene;
1-acetyloxy-2,4-diethoxy-3-methyl-6-chloronaphthalene;
1,2-diethoxy-3-methyl-4-acetyloxy-6-chloronaphthalene;
1-acetyloxy-2-t-butoxy-4-methoxynaphthalene;
1-methoxy-2-t-butoxy-4-acetyloxynaphthalene
1-propanoyloxy-2,4-dimethoxy-3-methyl-6-chloronaphthalene;
1,2-dimethoxy-3-methyl-4-propanoyloxy-6-chloronaphthalene
1-propanoyloxy-2-methyl-4-propoxynaphthalene; and
1-propoxy-2-methoxy-4-propanoyloxynaphthalene.

EXAMPLE 3

(Preparation of Compounds of Formula (Ie) and (If).)

A. A solution of 1-acetyloxy-2,4-diethoxynaphthalene (2.74 g) in 100 ml of methanol and 10 ml of water was stirred with 2.5 g of potassium carbonate for 6 hours. The solvent was then removed under reduced pressure, and the residue partitioned between ethyl acetate and water. The ethyl acetate layer was dried over anhydrous sodium sulfate and evaporated to a solid, which was recrystallized from ethyl acetate/hexane to give 1-hydroxy-2,4-diethoxynaphthalene, m.p. 83°-84° C.

B. Similarly, replacing 1-acetyloxy-2,4-diethoxynaphthalene with 1-acetyloxy-2,4-dimethoxynaphthalene, the following compound of formula (Ie) was prepared:

1-hydroxy-2,4-dimethoxynaphthalene, m.p. 87°-88° C.;

C. Similarly, replacing 1-acetyloxy-2,4-diethoxynaphthalene with other compounds of formula (Ic) or (Id), the following compounds of formula (Ie) and (If) are prepared:

1,2-diethoxy-4-hydroxynaphthalene;
1,2-dimethoxy-4-hydroxynaphthalene;
1-hydroxy-2,4-di-n-propoxynaphthalene;
1,2-di-n-propoxy-4-hydroxynaphthalene;
1-hydroxy-2-t-butoxy-4-methoxynaphthalene;
1-methoxy-2-t-butoxy-4-hydroxynaphthalene;
1-hydroxy-2,4-di-n-hexyloxynaphthalene;
1,2-di-n-hexyloxy-4-hydroxynaphthalene;
1-hydroxy-2,4-dimethoxy-3-methylnaphthalene;
1,2-dimethoxy-4-hydroxy-3-methylnaphthalene;
1-hydroxy-2,4-dimethoxy-3-t-butylnaphthalene;
1,2-dimethoxy-4-hydroxy-3,-t-butylnaphthalene;
1-hydroxy-2,4-dimethoxy-3-n-butylnaphthalene;
1,2-dimethoxy-4-hydroxy-3-n-butylnaphthalene;
1-hydroxy-2,4-dimethoxy-6-chloronaphthalene;
1,2-dimethoxy-4-hydroxy-6-chloronaphthalene;
1-hydroxy-2,4-diethoxy-6-ethylnaphthalene;
1,2-diethoxy-4-hydroxy-6-ethylnaphthalene;
1-hydroxy-2,4-diethoxy-6-phenylnaphthalene;
1,2-diethoxy-4-hydroxy-6-phenylnaphthalene;
1-hydroxy-2,4-di-n-propoxy-5-methoxynaphthalene;
1,2-di-n-propoxy-4-hydroxy-5-methoxynaphthalene;
1-hydroxy-2-methoxy-4-ethoxynaphthalene;
1-ethoxy-2-methoxy-4-hydroxynaphthalene;
1-hydroxy-2-ethoxy-4-methoxynaphthalene;
1-methoxy-2-ethoxy-4-hydroxynaphthalene;
1-hydroxy-2-methoxy-4-n-propoxynaphthalene;
1-n-propoxy-2-methoxy-4-hydroxynaphthalene;
1-hydroxy-2-ethoxy-4-n-hexyloxynaphthalene;
1-n-hexyloxy-2-ethoxy-4-hydroxynaphthalene;
1-hydroxy-2-n-pentyloxy-4-n-hexyloxynaphthalene;
1-n-hexyloxy-2-n-pentyloxy-4-hydroxynaphthalene;
1-hydroxy-2-phenoxy-4-methoxynaphthalene;
1-methoxy-2-phenoxy-4-hydroxynaphthalene;
1-hydroxy-2-methoxy-3-methyl-4-ethoxynaphthalene;
1-ethoxy-2-methoxy-3-methyl-4-hydroxynaphthalene;
1-hydroxy-2-ethoxy-4-methoxy-6-chloronaphthalene;
1-methoxy-2-ethoxy-4-hydroxy-6-chloronaphthalene;
1-hydroxy-2,6-dimethoxy-4-n-propoxynaphthalene; and
1-n-propoxy-2,6-dimethoxy-4-hydroxynaphthalene.

EXAMPLE 4

(Alternative Preparation of Compounds of Formula (Ie))

A. A solution of 18.9 g of 2-methoxynaphthoquinone in methanol was added slowly to a solution of 34.8 g of sodium hydrosulfite in methanol and the mixture stirred for 1 hour. The solvent was removed under reduced pressure and the residue partitioned between ethyl acetate and water. The organic layer was dried over anhydrous sodium sulfate and evaporated to purple solid. The solid was dissolved in 200 ml of methanol previously saturated with anhydrous hydrochloric acid and stirred for 3 minutes at 60° C. The mixture was then diluted with 200 ml of ice water and the precipitate filtered off, dried under vacuum and recrystallized from ether/pentane to give 13.25 g of 1-hydroxy-2,4-dimethoxynaphthalene, m.p. 87°-88° C.

B. Similarly 1-hydroxy-2,4-diethoxynaphthalene, m.p. 83°-84° C. was prepared.

C. Similarly, replacing 2-methoxynaphthoquinone with other compounds of formula (V), and following the procedure of paragraph A above, the following compounds of formula (Ie) are prepared:

1-hydroxy-2,4-dimethoxynaphthalene;
1-hydroxy-2,4-di-n-propoxynaphthalene;
1-hydroxy-2,4-di-n-butoxynaphthalene;
1-hydroxy-2,4-di-n-hexyloxynaphthalene;
1-hydroxy-2,4-dimethoxy-3-methylnaphthalene;
1-hydroxy-2,4-dimethoxy-3-n-butylnaphthalene;
1-hydroxy-2,4-dimethoxy-3-t-butylnaphthalene;
1-hydroxy-2,4-dimethoxy-6-chloronaphthalene;
1-hydroxy-2,4-dimethoxy-6-phenylnaphthalene;
1-hydroxy-2,4-diethoxy-6-ethylnaphthalene;
1-hydroxy-2,4-diethoxy-6-phenylnaphthalene;
1-hydroxy-2,4-di-n-propoxy-5-methoxynaphthalene; and
1-hydroxy-2,4-dibenzyloxynaphthalene.

What is claimed is:

1. A composition in a form suitable for optical administration for treating the condition of psoriasis which composition comprises a pharmaceutically acceptable, non-toxic carrier and a psoriasis relieving amount of a compound of the formula

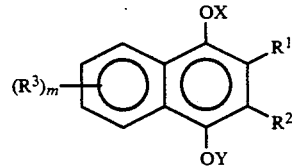

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are selected from the group consisting of hydrogen, $R^4$ and —C(O)W where if X is hydrogen, Y is not hydrogen, or if X is $R^4$, Y is not $R^4$, or if X is —C(O)W, Y is not —C(O)W; and wherein W is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^4$ is lower alkyl or phenyl-lower-alkyl, wherein the phenyl ring is optionally substituted by one or two substituents chosen from lower alkyl of one to four carbon atoms, lower alkoxy of one to four carbon atoms and halo.

2. The composition of claim 1, wherein $R^3$ is hydrogen, halo or lower alkyl.

3. The composition of claim 2, wherein $R^1$ is lower alkoxy and $R^2$ and $R^3$ are hydrogen.

4. The composition of claim 3, wherein X is —C(O)W and Y is lower alkyl.

5. The composition of claim 4, wherein $R^1$ and OY are the same and are methoxy or ethoxy and W is methyl, ethyl, t-butyl or phenyl.

6. The composition of claim 3, wherein X is hydrogen and Y is lower alkyl.

7. The composition of claim 6, wherein $R^1$ and OY are the same and are methoxy or ethoxy.

8. A method of treating psoriasis in mammals which comprises applying an effective amount of a compound of the formula

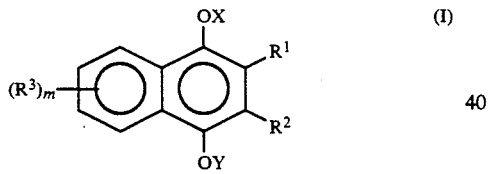

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are selected from the group consisting of hydrogen, $R^4$ and —C(O)W where if X is hydrogen, Y is not hydrogen, or if X is $R^4$, Y is not $R^4$, or if X is —C(O)W, Y is not —C(O)W; and wherein W is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^4$ is lower alkyl or phenyl-lower-alkyl, wherein the phenyl ring is optionally substituted by one or two substituents chosen from lower alkyl of one to four carbon atoms, lower alkoxy of one to four carbon atoms and halo.

9. A compound of the formula

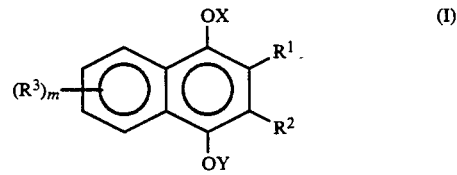

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one to two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are selected from the group consisting of hydrogen, $R^4$ and —C(O)W where if X is hydrogen, Y is not hydrogen, or if X is $R^4$, Y is not $R^4$, or if X is —C(O)W, Y is not —C(O)W; and wherein W is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^4$ is lower alkyl or phenyl-lower-alkyl, wherein the phenyl ring is optionally substituted by one or two substituents chosen from lower alkyl of one to four carbon atoms, lower alkoxy of one to four carbon atoms and halo;

with the proviso that X is not hydrogen or acetyl when $R^1$ is methoxy or ethoxy, $R^2$ and $R^3$ are hydrogen and that Y is methyl or ethyl, and Y is not hydrogen when X is methyl, $R^1$ is methoxy and $R^2$ and $R^3$ are hydrogen.

10. The compound of claim 9 in combination with its regioisomer.

11. The compound of claim 9, wherein $R^3$ is hydrogen, halo or lower alkyl.

12. The compound of claim 11, wherein one of X and Y is —C(O)W and the other X or Y is hydrogen.

13. The compound of claim 12, wherein $R^3$ is hydrogen.

14. The compound of claim 13, wherein W is lower alkyl of one to four carbon atoms or optionally substituted phenyl.

15. The compound of claim 14, wherein $R^1$ is methoxy or ethoxy and W is t-butyl or phenyl.

16. The compound of claim 11, wherein one of X and Y is —C(O)W and the other X or Y is lower alkyl.

17. The compound of claim 16, wherein $R^3$ is hydrogen.

18. The compound of claim 17, wherein W is lower alkyl of one to four carbon atoms or optionally substituted phenyl and $R^2$ is hydrogen.

19. The compound of claim 18, wherein $R^1$ and OX are the same or $R^1$ and OY are the same, and are methoxy ethoxy or n-propoxy.

20. The compound of claim 19, wherein X is —C(O)W, where W is ethyl, Y is methyl and $R^1$ is methoxy, namely 1-propanoyloxy-2,4-dimethoxynaphthalene.

21. The compound of claim 19, wherein X is methyl, Y is —C(O)W, where W is ethyl, and $R^1$ is methoxy, namely 1,2-dimethoxy-4-propanoyloxynaphthalene.

22. The compound of claim 20 in combination with its regioisomer of claim 21.

23. The compound of claim 19, wherein X is —C(O)W, where W is t-butyl, Y is methyl and $R^1$ is methoxy, namely 1-(2,2-dimethylpropanoyloxy)-2,4-dimethoxynaphthalene.

24. The compound of claim 19, wherein X is methyl, Y is —C(O)W, where W is t-butyl, and $R^1$ is methoxy, namely 1,2-dimethoxy-4-(2,2-dimethylpropanoyloxy)-naphthalene.

25. The compound of claim 23 in combination with tis regioisomer of claim 24.

26. The compound of claim 19, wherein X is —C(O)W, where W is phenyl, Y is methyl and $R^1$ is methoxy, namely 1-benzoyloxy-2,4-dimethoxynaphthalene.

27. The compound of claim 19, wherein X is methyl, Y is —C(O)W, where W is phenyl, and $R^1$ is methoxy, namely 1,2-dimethoxy-4-benzoyloxynaphthalene.

28. The compound of claim 26 in combination with its regioisomer of claim 27.

29. The compound of claim 19, wherein X is —C(O)W, where W is ethyl, Y is ethyl and $R^1$ is ethoxy, namely 1-propanoyloxy-2,4-diethoxynaphthalene.

30. The compound of claim 19, wherein X is ethyl, Y is —C(O)W, where W is ethyl, and $R^1$ is ethoxy, namely 1,2-diethoxy-4-propanoyloxynaphthalene.

31. The compound of claim 29 in combination with its regioisomer of claim 30.

32. The compound of claim 19, wherein X is —C(O)W, where W is t-butyl, Y is ethyl and $R^1$ is ethoxy, namely 1-(2,2-dimethylpropanoyloxy)-2,4-diethoxynaphthalene.

33. The compound of claim 19, wherein X is ethyl, Y is —C(O)W, where W is t-butyl, and $R^1$ is ethoxy, namely 1,2-diethoxy-4(2,2-dimethylpropanoyloxy)-naphthalene.

34. The compound of claim 32 in combination with its regioisomer of claim 33.

35. The compound of claim 19, wherein X is —C(O)W, where W is phenyl, Y is ethyl and $R^1$ is ethoxy, namely 1-benzoyloxy-2,4-diethoxynaphthalene.

36. The compound of claim 19, wherein X is ethyl, Y is —C(O)W, where W is phenyl, and $R^1$ is ethoxy, namely 1,2-diethoxy-4-benzoyloxynaphthalene.

37. The compound of claim 35 in combination with its regioisomer of claim 36.

38. The compound of claim 11, wherein one of X and Y is hydrogen and the other X or Y is lower alkyl.

39. The compound of claim 38, wherein $R^2$ and $R^3$ are hydrogen.

40. The compound of claim 39, wherein $R^1$ and OX are the same or $R^1$ and OY are the same, and are lower alkoxy of three to six carbon atoms.

41. The compound of claim 40 in combination with its regioisomer.

* * * * *